United States Patent
Chmiel et al.

(10) Patent No.: US 8,951,190 B2
(45) Date of Patent: Feb. 10, 2015

(54) TRANSFER FUNCTION CONTROL FOR BIOMETRIC MONITORING SYSTEM

(75) Inventors: Alan J. Chmiel, Avon Lake, OH (US); Bradley T. Humphreys, Lakewood, OH (US); Carlos M. Grodinsky, Hinkley, OH (US)

(73) Assignee: Zin Technologies, Inc., Middleburg Heights, OH (US)

( * ) Notice: Subject to any disclaimer, the term of this patent is extended or adjusted under 35 U.S.C. 154(b) by 813 days.

(21) Appl. No.: 11/686,667

(22) Filed: Mar. 15, 2007

(65) Prior Publication Data

US 2007/0179734 A1  Aug. 2, 2007

Related U.S. Application Data

(63) Continuation-in-part of application No. 11/236,899, filed on Sep. 28, 2005, now abandoned.

(51) Int. Cl.
- *A61B 5/00* (2006.01)
- *G01D 1/00* (2006.01)
- *G06F 15/00* (2006.01)
- *G06M 11/04* (2006.01)

(52) U.S. Cl.
CPC ............ *A61B 5/00* (2013.01); *A61B 5/7225* (2013.01); *A61B 2560/0443* (2013.01); *A61B 2560/0475* (2013.01)
USPC .......................................... 600/301; 702/127

(58) Field of Classification Search
CPC .... H03M 1/00; H03M 2201/4135–2201/4225; A61B 2560/0443; A61B 2560/0475
USPC .......................................... 600/300; 702/128
See application file for complete search history.

(56) References Cited

U.S. PATENT DOCUMENTS

| | | | |
|---|---|---|---|
| 3,972,320 A | | 8/1976 | Kalman |
| 4,301,333 A | * | 11/1981 | Gillette .................... 704/225 |
| 4,353,375 A | * | 10/1982 | Colburn et al. ............ 600/595 |
| 4,356,486 A | | 10/1982 | Mount |
| 4,494,950 A | | 1/1985 | Fischell |
| 4,566,461 A | * | 1/1986 | Lubell et al. .............. 600/481 |
| 4,667,682 A | * | 5/1987 | Ihlenfeld, III ............ 600/525 |
| 4,695,955 A | | 9/1987 | Faisandier |

(Continued)

FOREIGN PATENT DOCUMENTS

WO  WO 94/24929 A1  11/1994

OTHER PUBLICATIONS

"Register" definition, see "Ask a Scientist" dated back to Apr. 20, 2001 (pdf document is attached) http://web.archive.org/web/20010420191056/http://www.newton.dep.anl.gov/askasci/comp99/CS036.htm.*

(Continued)

*Primary Examiner* — William Thomson
*Assistant Examiner* — Shirley Jian
(74) *Attorney, Agent, or Firm* — Tarolli, Sundheim, Coveil & Tummino LLP

(57) ABSTRACT

A modular apparatus for acquiring biometric data may include circuitry operative to receive an input signal indicative of a biometric condition, the circuitry being configured to process the input signal according to a transfer function thereof and to provide a corresponding processed input signal. A controller is configured to provide at least one control signal to the circuitry to programmatically modify the transfer function of the modular system to facilitate acquisition of the biometric data.

17 Claims, 8 Drawing Sheets

(56) References Cited

U.S. PATENT DOCUMENTS

| | | | |
|---|---|---|---|
| 4,803,625 A * | 2/1989 | Fu et al. | 600/483 |
| 4,889,131 A | 12/1989 | Salem et al. | |
| 4,934,372 A | 6/1990 | Corenman et al. | |
| 4,938,228 A * | 7/1990 | Righter et al. | 600/503 |
| 4,958,645 A * | 9/1990 | Cadell et al. | 600/484 |
| 5,014,698 A | 5/1991 | Cohen | |
| 5,024,225 A * | 6/1991 | Fang | 600/301 |
| 5,050,612 A | 9/1991 | Matsumura | |
| 5,157,392 A * | 10/1992 | Zimmer | 340/853.9 |
| 5,300,093 A * | 4/1994 | Koestner et al. | 607/32 |
| 5,305,761 A * | 4/1994 | Byrne et al. | 600/510 |
| 5,307,263 A | 4/1994 | Brown | |
| 5,329,281 A * | 7/1994 | Baumgartner et al. | 341/139 |
| 5,365,066 A * | 11/1994 | Krueger et al. | 250/341.2 |
| 5,381,351 A * | 1/1995 | Kwong et al. | 702/88 |
| 5,417,222 A | 5/1995 | Dempsey et al. | |
| 5,430,843 A * | 7/1995 | Sato et al. | 709/225 |
| 5,458,123 A * | 10/1995 | Unger | 600/509 |
| 5,522,396 A | 6/1996 | Langer et al. | |
| 5,570,297 A * | 10/1996 | Brzezinski et al. | 358/1.13 |
| 5,601,435 A | 2/1997 | Quy | |
| 5,640,953 A | 6/1997 | Bishop et al. | |
| 5,701,894 A * | 12/1997 | Cherry et al. | 600/300 |
| 5,718,234 A * | 2/1998 | Warden et al. | 600/300 |
| 5,720,771 A | 2/1998 | Snell | |
| 5,738,104 A * | 4/1998 | Lo et al. | 600/521 |
| 5,759,199 A | 6/1998 | Snell et al. | |
| 5,787,187 A | 7/1998 | Bouchard et al. | |
| 5,831,673 A * | 11/1998 | Przyborski et al. | 348/239 |
| 5,832,448 A | 11/1998 | Brown | |
| 5,873,369 A | 2/1999 | Laniado et al. | |
| 5,876,350 A * | 3/1999 | Lo et al. | 600/519 |
| 5,891,042 A * | 4/1999 | Sham et al. | 600/483 |
| 5,899,855 A | 5/1999 | Brown | |
| 5,917,414 A | 6/1999 | Oppelt et al. | |
| 5,944,659 A | 8/1999 | Flach et al. | |
| 5,957,854 A | 9/1999 | Besson et al. | |
| 5,959,529 A | 9/1999 | Kail, IV | |
| 5,976,083 A * | 11/1999 | Richardson et al. | 600/300 |
| 6,018,677 A * | 1/2000 | Vidrine et al. | 600/520 |
| 6,115,629 A * | 9/2000 | Richter | 600/520 |
| 6,117,077 A | 9/2000 | Del Mar et al. | |
| 6,128,520 A * | 10/2000 | Minoz | 600/361 |
| 6,135,951 A * | 10/2000 | Richardson et al. | 600/300 |
| 6,161,095 A | 12/2000 | Brown | |
| 6,198,394 B1 | 3/2001 | Jacobsen et al. | |
| 6,238,338 B1 | 5/2001 | DeLuca et al. | |
| 6,246,992 B1 | 6/2001 | Brown | |
| 6,307,867 B1 * | 10/2001 | Roobol et al. | 370/470 |
| 6,334,073 B1 | 12/2001 | Levine | |
| 6,366,871 B1 * | 4/2002 | Geva | 702/188 |
| 6,381,577 B1 | 4/2002 | Brown | |
| 6,401,085 B1 * | 6/2002 | Gershman et al. | 707/4 |
| 6,430,436 B1 * | 8/2002 | Richter | 600/520 |
| 6,443,891 B1 | 9/2002 | Grevious | |
| 6,454,708 B1 * | 9/2002 | Ferguson et al. | 600/300 |
| 6,477,424 B1 | 11/2002 | Thompson et al. | |
| 6,516,289 B2 | 2/2003 | David | |
| 6,522,928 B2 | 2/2003 | Whitehurst et al. | |
| 6,540,672 B1 | 4/2003 | Simonsen et al. | |
| 6,549,756 B1 * | 4/2003 | Engstrom | 455/66.1 |
| 6,551,252 B2 * | 4/2003 | Sackner et al. | 600/536 |
| 6,572,542 B1 | 6/2003 | Houben et al. | |
| 6,574,509 B1 | 6/2003 | Kraus et al. | |
| 6,587,840 B1 * | 7/2003 | Smith et al. | 705/35 |
| 6,599,241 B1 | 7/2003 | Murphy | |
| 6,606,993 B1 | 8/2003 | Wiesmann | |
| 6,612,984 B1 | 9/2003 | Kerr, II | |
| 6,616,613 B1 | 9/2003 | Goodman | |
| 6,635,016 B2 | 10/2003 | Finkelshteins | |
| 6,641,533 B2 * | 11/2003 | Causey et al. | 600/300 |
| 6,647,298 B2 | 11/2003 | Abrahamson et al. | |
| 6,689,117 B2 | 2/2004 | Sweeney et al. | |
| 6,712,762 B1 | 3/2004 | Lichter et al. | |
| 6,738,671 B2 | 5/2004 | Christophersom et al. | |
| 6,748,250 B1 | 6/2004 | Berman et al. | |
| 6,768,920 B2 | 7/2004 | Lange et al. | |
| 6,773,396 B2 | 8/2004 | Flach et al. | |
| 6,779,066 B2 | 8/2004 | Sakamoto | |
| 6,780,156 B2 * | 8/2004 | Haueter et al. | 600/459 |
| 6,786,873 B2 | 9/2004 | Zoth et al. | |
| 6,790,178 B1 | 9/2004 | Mault et al. | |
| 6,837,118 B2 * | 1/2005 | Bonne et al. | 73/863.12 |
| 6,847,892 B2 * | 1/2005 | Zhou et al. | 701/213 |
| 6,850,788 B2 | 2/2005 | Al-Ali | |
| 6,856,832 B1 | 2/2005 | Matsumura et al. | |
| 6,889,165 B2 * | 5/2005 | Lind et al. | 702/183 |
| 6,904,408 B1 * | 6/2005 | McCarthy et al. | 705/2 |
| 6,936,029 B2 * | 8/2005 | Mann et al. | 604/131 |
| 6,985,078 B2 | 1/2006 | Suzuki et al. | |
| 7,003,228 B2 * | 2/2006 | Wang et al. | 398/85 |
| 7,034,677 B2 * | 4/2006 | Steinthal et al. | 340/539.12 |
| 7,215,991 B2 * | 5/2007 | Besson et al. | 600/509 |
| 7,292,169 B2 * | 11/2007 | Mori et al. | 341/139 |
| 7,294,105 B1 * | 11/2007 | Islam | 600/300 |
| 7,352,310 B2 * | 4/2008 | Mori et al. | 341/139 |
| 7,363,398 B2 * | 4/2008 | Scott | 710/52 |
| 7,382,296 B2 * | 6/2008 | Delanghe et al. | 341/118 |
| 2001/0039373 A1 | 11/2001 | Cunningham et al. | |
| 2001/0056225 A1 | 12/2001 | DeVito | |
| 2002/0002334 A1 * | 1/2002 | Okuno et al. | 600/443 |
| 2002/0013518 A1 | 1/2002 | West et al. | |
| 2002/0049371 A1 | 4/2002 | Lai et al. | |
| 2002/0082665 A1 | 6/2002 | Haller et al. | |
| 2002/0128804 A1 * | 9/2002 | Geva | 702/188 |
| 2003/0004403 A1 * | 1/2003 | Drinan et al. | 600/301 |
| 2003/0065536 A1 * | 4/2003 | Hansen et al. | 705/2 |
| 2003/0088160 A1 | 5/2003 | Halleck et al. | |
| 2003/0122677 A1 | 7/2003 | Kail, IV | |
| 2003/0144711 A1 | 7/2003 | Pless et al. | |
| 2003/0171789 A1 | 9/2003 | Malek et al. | |
| 2003/0212441 A1 | 11/2003 | Starkweather et al. | |
| 2004/0002634 A1 | 1/2004 | Nihtila | |
| 2004/0015551 A1 * | 1/2004 | Thornton | 709/204 |
| 2004/0030226 A1 | 2/2004 | Quy | |
| 2004/0049246 A1 | 3/2004 | Almendinger et al. | |
| 2004/0059396 A1 | 3/2004 | Reinke et al. | |
| 2004/0078219 A1 * | 4/2004 | Kaylor et al. | 705/2 |
| 2004/0080526 A1 * | 4/2004 | Thornton | 345/721 |
| 2004/0082840 A1 | 4/2004 | Chen | 600/300 |
| 2004/0083302 A1 * | 4/2004 | Thornton | 709/231 |
| 2004/0087865 A1 * | 5/2004 | Kelly | 600/508 |
| 2004/0093239 A1 | 5/2004 | Ott et al. | |
| 2004/0107766 A1 * | 6/2004 | Bonne et al. | 73/25.05 |
| 2004/0116908 A1 | 6/2004 | Birkenbach et al. | |
| 2004/0147980 A1 | 7/2004 | Bardy | |
| 2004/0148199 A1 | 7/2004 | Dixon, Jr. | |
| 2004/0162466 A1 | 8/2004 | Quy | |
| 2004/0186388 A1 * | 9/2004 | Gerasimov | 600/519 |
| 2004/0199056 A1 | 10/2004 | Husemann et al. | |
| 2004/0218789 A1 | 11/2004 | Polcha et al. | |
| 2004/0225203 A1 | 11/2004 | Jemison et al. | |
| 2004/0236189 A1 | 11/2004 | Hawthorne et al. | |
| 2005/0008070 A1 * | 1/2005 | Wang et al. | 375/232 |
| 2005/0021370 A1 | 1/2005 | Riff et al. | |
| 2005/0043767 A1 | 2/2005 | Belaclcazar | |
| 2005/0101841 A9 * | 5/2005 | Kaylor et al. | 600/300 |
| 2005/0101875 A1 | 5/2005 | Semler et al. | |
| 2005/0113703 A1 | 5/2005 | Farringdon et al. | |
| 2005/0119581 A1 | 6/2005 | Matsumura et al. | |
| 2005/0119833 A1 * | 6/2005 | Nanikashvili | 702/19 |
| 2005/0165323 A1 | 7/2005 | Montgomery et al. | |
| 2005/0171410 A1 | 8/2005 | Hjelt et al. | |
| 2005/0171444 A1 | 8/2005 | Ono et al. | |
| 2005/0182306 A1 | 8/2005 | Sloan | |
| 2005/0192488 A1 | 9/2005 | Bryenton et al. | |
| 2005/0203349 A1 * | 9/2005 | Nanikashvili | 600/300 |
| 2005/0206518 A1 | 9/2005 | Welch et al. | |
| 2005/0228234 A1 | 10/2005 | Yang | |
| 2005/0228245 A1 | 10/2005 | Quy | |
| 2005/0228301 A1 | 10/2005 | Banet et al. | |
| 2005/0234313 A1 | 10/2005 | Rowlandson et al. | |
| 2005/0245992 A1 | 11/2005 | Persen et al. | |
| 2005/0245995 A1 | 11/2005 | Diebold | |

(56) References Cited

U.S. PATENT DOCUMENTS

| | | |
|---|---|---|
| 2005/0249037 A1 | 11/2005 | Kohn et al. |
| 2005/0250996 A1 | 11/2005 | Shirai et al. |
| 2005/0251218 A1 | 11/2005 | Markowitz et al. |
| 2005/0272984 A1 | 12/2005 | Huiku |
| 2005/0273509 A1 | 12/2005 | Brown |
| 2005/0277844 A1 | 12/2005 | Strother et al. |
| 2005/0288563 A1 | 12/2005 | Feliss et al. |
| 2006/0004266 A1 | 1/2006 | Shirai et al. |
| 2006/0010090 A1 | 1/2006 | Brockway et al. |
| 2006/0020178 A1 | 1/2006 | Sotos et al. |
| 2006/0020301 A1 | 1/2006 | Hanson et al. |
| 2006/0025663 A1 | 2/2006 | Talbot et al. |
| 2006/0030759 A1 | 2/2006 | Weiner et al. |
| 2006/0030760 A1 | 2/2006 | Geiger |
| 2006/0030891 A1 | 2/2006 | Saltzstein et al. |
| 2006/0031102 A1 | 2/2006 | Teller et al. |
| 2006/0031378 A1 | 2/2006 | Vallapureddy et al. |
| 2006/0078171 A1 | 4/2006 | Govindaraju et al. |
| 2006/0204047 A1 | 9/2006 | Dave et al. |
| 2007/0055120 A1* | 3/2007 | Juan ............................... 600/392 |
| 2007/0055166 A1* | 3/2007 | Patil ............................... 600/509 |
| 2007/0109170 A1* | 5/2007 | Mori et al. ..................... 341/155 |
| 2007/0229333 A1* | 10/2007 | Mori et al. ..................... 341/139 |

OTHER PUBLICATIONS

International Search Report Appl. No. PCT/US06/36674, Date mailed: Aug. 3, 2007.

Written Opinion of the International Search Authority, Date mailed Aug. 3, 2007.

International Search Report Appl. No. PCT/US08/57037, Date mailed: Oct. 2, 2008.

Written Opinion of the International Searching Authority for Appl. No. PCT/US08/57037, Date mailed Oct. 2, 2008.

Supplementary European Search Report, Sep. 30, 2013, Zin Technologies, Inc.

\* cited by examiner

TRANSFER FUNCTION CONTROL FOR BIOMETRIC MONITORING SYSTEM

RELATED APPLICATION

This application is a continuation-in-part of U.S. patent application Ser. No. 11,236,899, which was filed on Sep. 28, 2005 now abandoned, and entitled COMPACT WIRELESS BIOMETRIC MONITORING AND REAL TIME PROCESSING SYSTEM, the entire contents of which application is incorporated herein by reference.

GOVERNMENT INTEREST

The subject invocation is being developed with government support under Contract No. NNC05CA65C awarded by NASA. The United States government may have certain rights in the innovation.

BACKGROUND

Diagnosis of ailments and treatment of disease often requires an analysis of biological signs obtained from a patient in the course of normal activity over a period of time. Personal health monitors are commonly employed to gather data related to a patients biometric data.

In general, a personal health monitor is a device used to measure and record one or more clinical parameters of a patient for later transmission to the patient's physician or other health care provider. The personal health monitor may be used in a hospital or clinical setting as an adjunct to existing care. Additionally, the personal health monitor may also be used by the patient outside care facilities (e.g., at a patient's home). When used by a patient at home, the patient operates the personal health monitor to record certain bodily clinical parameters. The personal health monitor can be used by the patient who has a condition requiring monitoring of one or more clinical parameters, but who otherwise may not require the level of care such as provided by a hospital. Accordingly, the personal health monitor provides potential savings in medical costs involved with a hospital stay.

For example, continuously monitoring cardiac patients immediately following coronary attacks is important. Such is normally accomplished effectively in the coronary care unit of most hospitals where the patients are continuously monitored following heart attacks to detect arrhythmias of the heart, for example monitoring and warning for ventricular arrhythmias, which may lead to ventricular fibrillation and death. Through prompt recognition and treatment of such warnings related to ventricular arrhythmias in coronary care units, the mortality rate of acute myocardial infarctions has been reduced considerably. In addition, many post myocardial infarction cardiac patients continue to have frequent ventricular extra systoles after discharge from the hospital. Accordingly, it is desired to continuously monitor the patient over a certain period of time and under varying conditions of stress, to determine the effectiveness treatment which has been introduced, such as the proper dosage of medication.

Constant monitoring of such patients after release from the hospital may be difficult because of the logistics involved, and particularly since they can no longer be monitored closely as a group by direct wiring or close telemetry, as commonly implemented in hospital settings. As a result, various systems have been developed to attempt to monitor the ECG signals of out-patients to thereby provide a diagnostic tool for additional treatment or variation of treatment for the patients as may be required. Accordingly, there has been a persistent need to develop health monitoring systems and methods that can effectively alert medical personnel when a patient needs medical assistance.

Nevertheless, such mobile units are typically spacious and difficult to set up and maintain. Moreover, in general these units are not suitable for readily monitoring a plurality of biological signs and biometric conditions. In addition, such systems lack flexibility during usage as they typically have fixed sensor types and configurations.

At the same time, compatibility of such systems with various communication requirements and protocols can create further problems and increase costs. This can further hinder a quick response of the medical staff when health issues arise for an ambulatory patient who employs such monitors. Also, with the current limits in resolution on existing biometric data acquisition modules, the analysis of low magnitude (and sometimes long duration) biometric parameters (e.g., EKG activity) is typically hindered and/or not possible. Such problem is further compounded due to gain amplifiers lack of operation flexibility, wherein the gain amplifiers (e.g., associated with sensors) are commonly set for high exertion activity levels.

SUMMARY

The present invention relates generally to transfer function control for a biometric monitoring system and to a related method.

One aspect of the invention provides a modular apparatus for acquiring biometric data. The modular apparatus may include circuitry operative to receive an input signal indicative of a biometric condition, the circuitry being configured to process the input signal according to a transfer function thereof and to provide a corresponding processed input signal. A controller is configured to provide at least one control signal to the circuitry to programmatically modify the transfer function of the modular system to facilitate acquisition of the biometric data.

Another aspect of the invention provides a modular system for acquiring biometric data. The system includes means for amplifying an input signal indicative of a sensed biometric condition to provide an amplified signal. The system also includes means for processing the amplified signal to provide a computed value representative of the sensed biometric condition. The system also includes means for controlling a transfer function of at least the means for amplifying based on the computed value.

Yet another aspect of the invention provides a method for controlling at least one channel transfer function for a modular unit. The modular unit includes at least one channel configured to receive at least one input signal indicative of a sensed biometric condition. The method includes initializing at least one channel transfer function parameter for circuitry of the at least one channel. The at least one input signal is processed by the circuitry of the at least one channel. The at least one input signal is processed by the circuitry according to the at least one channel transfer function parameter. The processed input signal is further analyzed to determine an adjustment to the at least one transfer function parameter based on the processed input signal. The at least one channel transfer function parameter is dynamically adjusted based on the analyzed processed input signal being outside of expected operating parameters.

DETAILED DESCRIPTION

Figure 1:
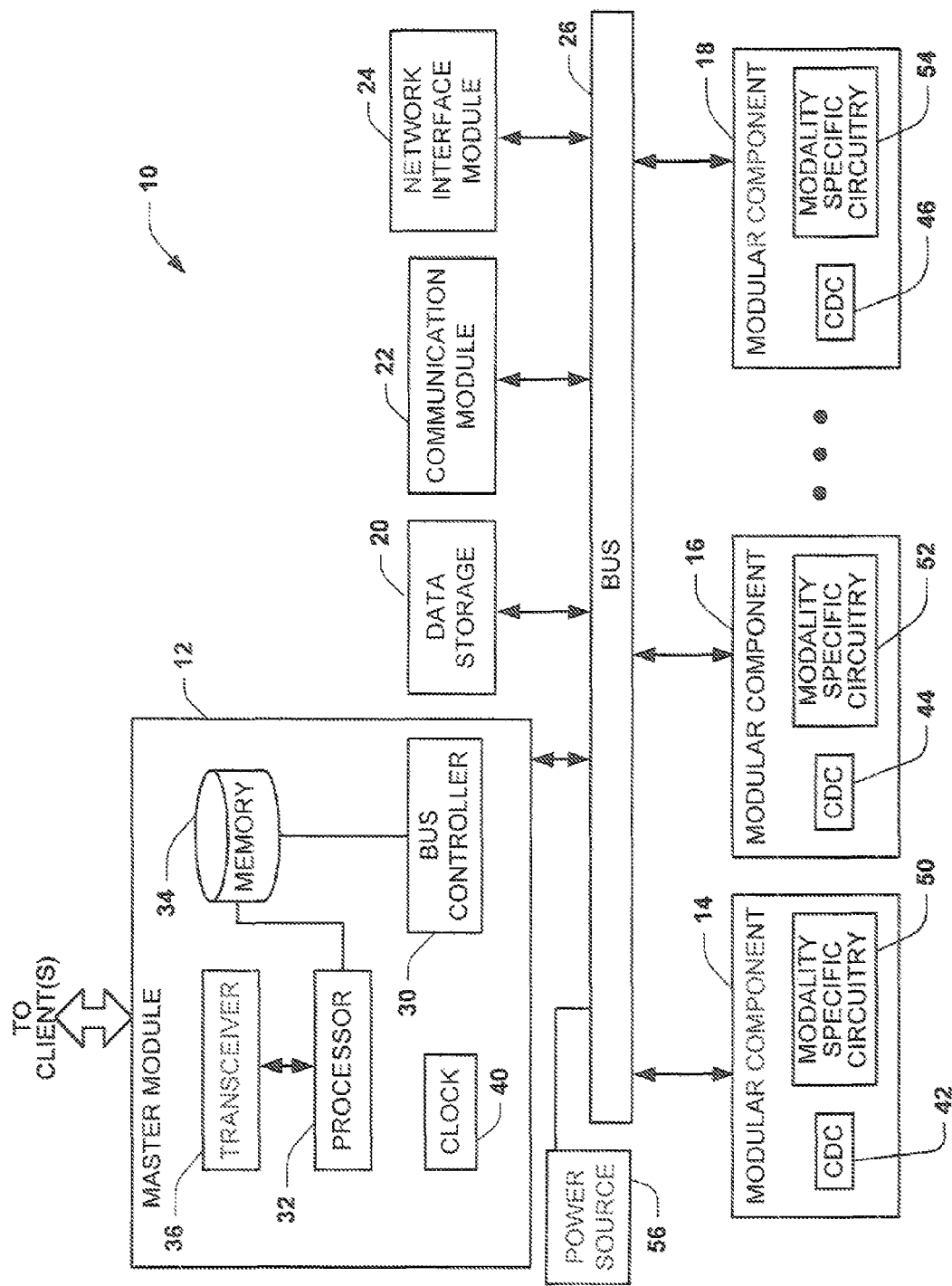
FIG. 1 depicts an example of a system that can be employed to acquire biometric data according to an aspect of the present invention.

FIG. 1 depicts an example of a system 10 that can be utilized to acquire biometric data. As used herein, the term "biometric data" or related phrases (e.g., "biometric parameter" and "biometric information") is intended to encompass biological or biomedical information required from one or more sensors. Biometric data can also relate to information associated with controlling the delivery of a therapy being delivered to a patient or it can also represent information associated with controlling drug delivery equipment or sensor equipment or operating parameters associated with sensor status and operation that may be employed in connection with the acquisition of data or control of therapy devices.

The system 10 includes a plurality of modules. In the example of FIG. 1, the system 10 includes a master module 12 and a plurality of other modular components 14, 16, 18, 20, 22 and 24. Each of the respective modules 12-24 can be programmed and/or configured according to the intended use of the system 10. At least some of modular components 14, 16, 18, 20, 22 and 24 can be replaced, inserted and/or swapped for to achieve a desired aggregate function, such as can include collection of biometric parameters, control of desired therapy, communication of data to and from the system 10 or any combination thereof.

For example, a clinician can determine a customized routine for acquisition of biometric data and or therapy. Based on the routine, the clinician can determine which types of modules should be inserted into the system as the modular components 12-24. For instance, the modular components 14 and 16 can be configured to acquire biometric data associated with a patient and the modular component 18 can deliver a desired type of therapy (e.g., electrical and/or chemical).

By way of further example, the modular component 14 can measure one or more biometric parameters, and/or supply input that is representative of the status of a controlled process. The input can be provided to the master module 12 or another module component 18, such as can be configured to change one or more outputs for effecting control of the therapy process. For instance, one or more of the modular components 12, 14 and 16 can supply activation commands to a glucose pump in a patient's proximity, such as when acquired data that pertains to blood sugar of a patient indicates a critical level. Similarly, muscle tension can be employed as a biometric condition to be collected by a modular component, and employed for delivery of chemical or electrical therapy to perform muscle relaxation by the same or a different modular component to a patient. The inputs and outputs of each of the modular component can be binary, (e.g., on or off), and/or analog assuming a continuous range of values.

Each of the respective modules 12-24 can communicate over a data bus or backplane 26. For example, the bus 26 can enable communication between the master module 12 and any of the other modules 14-24. Additionally or alternatively, each of the modules 12-24 can communicate with each other over the bus 26. Those skilled in the art will understand and appreciate various types of buses or communication links and communications protocols that can be utilized to provide for communication between the respective modules 12-24.

The system 10 can be considered a distributed computing arrangement since certain processing functions can be distributed to the respective modules 14-24. In this way, computing power requirements of the master module 12 can be reduced based upon the portions of processing being implemented at the respective components 14-24. In this respect, the power usage of the system can be scaled to the medically desired configuration of the system. By way of further example, each of the modules 14, 16 and 18 can correspond to a modular apparatus that can be utilized to acquire biometric data that can be transmitted to the master module 12 for aggregate communication to one or more clients, such as a Personal Digital Assistant (PDA), computer, workstation, a server and the like.

In the example of FIG. 1, the master module 12 can include a bus controller 30 that can be utilized to control data communication over the bus 26. For instance, the bus controller 30 can transmit data from the master module 12 to the respective modular components 14 through 24 via the bus 26. As one example, the master module 12 can provide respective program instructions to one or more of the modules 14 through 24 for controlling operation and the particular function being performed by the respective module(s). This can include setting one or more operating parameters as well as defining the specific functions being performed by the respective components. The bus controller 30 can also control the rate at which each of the respective modules may communicate data over the bus 26. For example, the bus controller 30 can control rate at which data is sent from each of the respective modules 14-24 to the master module (e.g., corresponding to a data acquisition rate for the master module) synchronously or asynchronously.

The master module 12 also includes a processor 32 that can execute program instructions stored in associated memory 34. For example, the memory 34 can store executable instructions that control high level functions of the bus controller 30 to facilitate and optimize traffic over the bus 26. The processor 32 can also control other functions associated with the system 10 such as communication to one or more clients through a respective transceiver 36. The transceiver 36 can be implemented as a wired or wireless type of communication device. Those skilled in the art will understand and appreciate various types of transceivers that can be utilized to transmit and/or receive data.

For instance, the processor can transfer data from the memory to the associated client via the transceiver 36. Alternatively, the client may be configured to access and download data from selected portions of the memory 34. For example, the client can run an appropriate user interface (not shown) to initiate or terminate or otherwise control one or more functions associated with operation of the system 10.

The master module 12 can also include a clock 40 that is used to control timing associated with operation of the master module 12 control the timing associated with data transfer over the bus 26 via the bus controller 30. The master module can also employ the clock 40 to control internal operation of the master module, including communication via the transceiver 36. The transceiver 36 further can be utilized for programming operation of the system 10 through an appropriate input/output port.

The memory 34 can be implemented as including one or more different types of memory, such as volatile or nonvolatile memory. The memory can be accessed by the processor 32 for storing executable instructions for controlling operation of the master module 12 and the system 10, more generally. The memory 34 can also be utilized to store data that is provided to the master module via the transceiver 36 or bus controller 30. For example, the memory 34 can be utilized as a temporary data storage device for biometric data and control information that may be received from any of the other respective modules 14 through 24 via the bus 26.

The system 10 can further include a data storage module 20 that can be utilized for storing addition data that is transmitted over the bus 26. For example, the processor 32 can store data to the data storage module 20. Additionally or alternatively, the data storage module 20 can be implemented as a modular component similar to the other modules 12-18, 22 and 24 in the system 10. For example, a module having a desired memory capacity can be connected to the bus as the data storage module 20 to increase the storage capacity of the system 10. This would allow the data storage function of the other the modular components 12-18, 22 and 24 to be distributed to the data storage module, further increasing the cost efficiency associated with such modules since such modules can be configured with reduced memory requirements. A client thus may be able to access and retrieve data from the data storage module via the master module (through the transceiver 36, processor 32 and the bus controller 30) and bus 26.

The client may also communicate with the data storage module 20 or other modules 12-18, 22 and 24 in the system 10 by other communication devices. For example, the system 10 can include addition means of communicating to one or more external devices, such as a communications module 22. For example, the communication module 22 can correspond to a wireless communication module. The wireless communication module 22, for example, can transmit according to any one of a variety of known wireless protocols, such as an 802.11x standard, Bluetooth, cellular communications and the like.

Additionally or alternatively, the system 10 can include a network interface module 24 that can be programmed and/or configured to connect to a computer network, such as a local area network (LAN) or a wide area network (WAN) such as the internet. As one example, the network interface module 24 can be electrically connected to the network via a standard network connection. The network interface module 24 thus can provide an appropriate connection with the desired network. Thus, in the example of FIG. 1, communications can be implemented over the bus 26 via the bus controller 30, over the bus through the network interface module 24 and over the bus via the communication module 22. In this way data can be transmitted to and received from the system 10 via the network interface module 24.

In the example of FIG. 1, the modular components 14, 16 and 18 can be programmed and/or configured based on the requirements of the biometric condition(s) that is to be measured and/or other functions that are to be controlled, such as including the administration of a desired therapy. Each of the respective components 14, 16 and 18 can includes a common architecture, which corresponds to circuitry referred to herein as a common data controller (CDC) 42, 44 and 46. As one example, each of the CDCs 42, 44 and 46 can be a common architecture that includes a processor or controller and other circuitry that is configured to control operation of the modular component as well as facilitate communication to and from the respective modular component via the bus 26.

Each of the modular components 14, 16 and 18 also includes modality specific circuitry 50, 52 and 54. The modality specific circuitry can vary according to the type of biometric condition data that is to be acquired by a respective module and/or the type of therapy that might be delivered by the respective module. That is, the modality specific circuitry 50, 52 and 54 of each of the modules 14, 16 and 18 is programmed and/or configured to perform a predetermined biometric function (e.g., sensing or therapeutic function—a/k/a modality). For instance, one or more of the modules 14, 16 and 18 can be configured to acquire a predetermined type of biometric condition data by sensing biometric or biological conditions of a patient. By way of further example, each of the modality specific circuitry 50, 52 and 54 can be adapted to acquire data related to the modalities of electromyography (EMG), electrocardiography (ECG), electroencephalography (EEG), plantar pressure, joining angle, pulse oximetry, blood pressure, core body temperature, blood glucose, and the like. Additionally or alternatively, one or more other modules 14, 16 and 18 can be configured to administer a desired therapy (e.g., electrical or chemical therapies).

Thus, each of the modality specific circuitry 50, 52 and 54 includes circuitry operative to receive an input signal indicative of a biometric condition. As described herein, such input signal indicative of the biometric condition can correspond to a signal representing a sensed biometric condition of the patient. Alternatively, in other circumstances, the input signal can be a signal (e.g., feedback signal) associated with a delivery of a therapy to the patient, such as may be in the from of chemical or electrical therapies.

Advantageously, the particular combination of data acquisition and/or therapy administration thus can be tailored on a patient-by-patient basis by interchanging or swapping various modular components, having different modality specific circuitry, into or out of the system 10. As described herein, each of the modular components 12-24 can have a form factor, which may be a standard or proprietary form factor, which is dimensioned and configured for swappable connection into the system. Thus, as the intended use of the system changes, different modules can be replaced or swapped for other modules so that the aggregate system meets the needs for particular patient. For example, the respective connections between the modules 12-24 and the bus are schematically represented as bi-directional arrows. Such connections enable data communication from a given one of the respective modules to one or more other modules over the bus 26, such as under the control of the bus controller 30 in the master module 12. Additionally, the connections can provide power to each of the respective modules 12-24. For instance, a power source 56, such as including a voltage regulator and one or more batteries) can distribute power to each of the respective modules via the bus 26. Alternative power systems can be utilized to provide power, such as may be implemented by separate power connection or in one or more of modules 12-24.

Each of the modular components 14, 16 and 18 (whether it is sensing biometric condition of a patient or controlling delivery of a therapy) operates according to a transfer function. The transfer function of the modular component can be derived as the aggregate (e.g., by convolution) of transfer functions for circuitry that forms each of the modular components. For instance, each channel of the modality specific circuitry 50, 52, and 54 can include several different circuit components, each having a unique component transfer function, which collectively determines the channel transfer function for a respective channel of the modality specificity circuitry. Moreover, a given modular component can include a plurality of channels, each of which channels can be represented as a separate channel transfer function. Each of the channel transfer functions can be adjusted dynamically to improve performance, such as by adjusting one or more component transfer functions.

By way of example, a given channel of a modality specific circuit 50, 52 and 54 can include an analog input circuit configured to process a received input signal according to an associated transfer function and to provide a corresponding processed input signal. The modality specific circuit can include additional filtering and amplifier stages, which also can be represented as respective transfer functions, and provide amplified and filtered output signals according to their respective transfer functions. Additionally conversion to a digital signal and subsequent digital processing stages can also be represented by corresponding transfer functions. Thus, the transfer function associated with the different stages or circuit parts in the modality specific circuitry cooperate to define the plant transfer function for each channel and each modular component 14, 16, 18 as a whole.

The CDC 42, 44 and 46 is configured to provide one or more control signals to the modality specific circuitry 50, 52 and 54, respectively, to modify the transfer function characteristics of the modular component. For instance each CDC 42, 44 and 46 can dynamically modify the transfer function associated with each given channel of the respective modality specific circuitry. As one example, the CDC can adjust the transfer function for a given channel so that a maximum resolution of the sensor can be achieved according to the dynamic range of the circuitry.

By way of further example, each CDC can include a register (not shown) that is configured for storing a digital value representing the corresponding input signal that has been processed by the modality specific circuitry. The CDC can adjust the transfer function of the modality specific circuitry such that the maximum resolution of the sensor can be represented with maximum number of bits available in the register. In this way, the biometric condition data can be acquired with a substantially maximum resolution according to dynamic range of the data acquisition circuitry and the available register memory in which the data is stored. For instance, the CDC can adjust the transfer function by changing the gain or one or more amplifiers of the modality specific circuitry so that the signal value that is accommodated in the register with a substantially maximum resolution according to the dynamic range of the circuitry.

Figure 2:
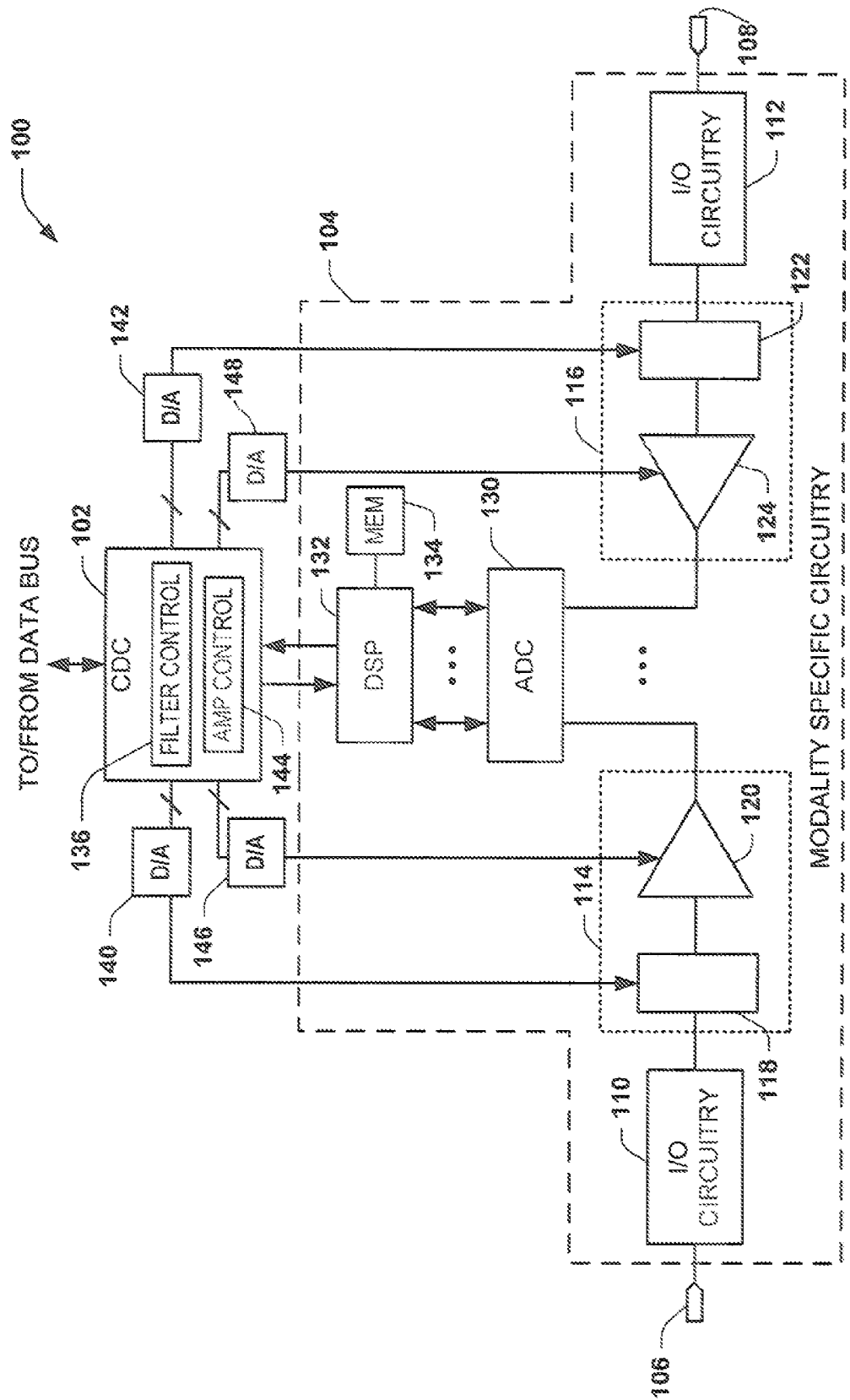
FIG. 2 depicts an example block diagram of a modular apparatus that can be implemented according to an aspect of the present invention.

FIG. 2 depicts an example of a modular apparatus 100 that can be implemented according to an aspect of the present invention. The modular apparatus 100 includes a CDC 102 that is electrically coupled with modality specific circuitry 104. The modular apparatus 100 can be self contained within a module having a preconfigured form factor, which can vary according to system requirements, such as including the examples shown and described herein. The modality specific circuitry 104 includes one or more inputs or outputs that can be electrically coupled to respective sensors or therapy delivery devices (not shown). The respective ports for connection to the sensor or therapy delivery devices are indicated schematically at 106 or 108. While two such ports 106 and 108 are depicted in the example of FIG. 2, it will be understood and appreciated that there could be any number of one or more such ports for connecting with appreciated that there could be any number of one or more such ports for connecting with appropriate sensors or therapy delivery devices. Each port 106 and 108 thus defines a respective channel of the modular apparatus 100 that can be represented in conjunction with other circuitry as a corresponding channel transfer function.

For purposes of consistency, in the example of FIG. 2 each of the respective ports 106 and 108 is illustrated as a corresponding sensor input port that can receive a sensor input signal, such as from an associated sensor (not shown). The characteristics (e.g., frequency and amplitude) of the input signal received at 106 and 108 thus can vary according to the type of biometric condition being sensed. The modality specific circuitry 104 includes corresponding analog input circuitry 110 and 112 that is associated with each input port for providing isolation and analog pre-processing the respective input signal. Those skilled in the art will understand and appreciate various types of input circuits (e.g., isolation amplifiers) that can be utilized to receive signals from appropriate sensors and provide corresponding input signals. The input circuitry 110 and 112 in the modality specific circuitry thus can vary according to the modality and the biometric conditions intended to be monitored by the modular apparatus 100. Alternatively, the analog circuitry 110 and 112 might correspond to output or control circuitry (e.g., drivers) configured to control delivery of appropriate therapies, such as a chemical or electrical based therapies. The analog circuitry 110 and 112 further can provide for isolation between the leads and sensors connected as the ports 106 and 108 and the other processing performed by the modality specific circuitry 104.

Each of the circuits 110 and 112 provides corresponding analog outputs signals to filter networks 114 and 116, respectively. In the example of FIG. 2, the filter network 114 includes a filter block 118 and an amplifier block 120 and the filtered network 116 includes a filter block 122 and amplifier block 124. It should be understood and appreciated that each of the respective filters 118 and 122 can include any number of one or more filters that can be represented as a corresponding transfer function with poles and zeros and respective filter coefficients. Additionally, each of the amplifiers 120 and 124 can include any number of one or more amplifiers that can be represented by a corresponding transfer function that represent the gain implemented by the amplifiers. Additionally, while the schematic depiction of the filter networks 114 and 116 shows a filter stage followed by an amplifier stage, there can be various arrangements, orders, and combinations of amplifier and filter stages to provide the filter networks.

The filter network 114 and 116 can be programmable, such as based on control signals from the CDC 102. For example, the filter coefficients of the filter blocks 118 and 122 can be programmed. Additionally, or alternatively, the gain of the respective amplifiers 120 and 124 can be programmed. That is, the amplifier block 120 and 124 can be implemented as programmable gain amplifiers. The filter networks 114 and 116 that can perform associated filtering and amplification of the analog input signals (from the analog input circuitry 110 and 112) and provide corresponding filtered and amplified signals to an analog-to-digital converter (ADC) 130. As one example, the ADC 130 can be implemented as a Sigma-Delta ($\Sigma\Delta$) ADC that operates on each of the respective channels to provide a corresponding high-resolution digital representation of the filtered and amplified signals. Thus, the ADC 130 provides a corresponding digital output signal for each respective channel of the modality specific circuitry 104.

The respective digital outputs for each channel are provided to a digital signal processor (DSP) 132. The digital outputs can be provided as separate connections (e.g., parallel outputs) of the ADC 130 or the digital output can be provided via a corresponding bus or other communication link. The DSP 132 is connected with memory 134. For example, the memory 134 can contain executable instructions that cause the DSP to compute a predetermined function on the digital representation for each of the filter and amplified channel inputs. The respective function can be a linear function or a nonlinear function according to the type and content of the data received at the respective inputs 106 and 108. The function computed by the DSP for each channel of the apparatus 100, for example, can be determined according to the transfer function associated with each respective channel of the apparatus 100 of the modular apparatus 100. Thus, the functions being computed by the DSP for each channel of the apparatus 100 can be the same or different. The DSP 132 provides corresponding computed values as outputs to the CDC 102. The CDC 102 can also control the function computed by the DSP (or other operations of the DSP), such as by providing program instructions that can be stored in the memory 134. For example, the CDC 102 can modify the functions at run time, such as during normal operation or during a programming mode of the modular apparatus 100.

For example, the CDC 102 can provide one or more control signals to each of the filter networks 114 and 116 to adjust the transfer function associated with each respective channel. The CDC 102 can adjust gain according to the dynamic range of each respective channel and the associated data acquisition device. As mentioned above, the transfer function associated with a given channel can include a representation of operating characteristics associated with the circuitry 110 or 112 as well as the respective filter network 114 and 116. The transfer function of a channel can also represent operation of the ADC 130 (e.g., the latency through the sigma delta modulator) as well as include poles and/or zeros representing the signal processing performed by the DSP 132. The respective components of each individual channel transfer function thus can be convolved to provide an aggregate transfer function channel ($H_{CH}$), such as follows:

$$H_{CH}=H_1+H_2+H_3\ldots H_N$$

where $H_1$ through $H_N$ represent the individual component channel transfer function components of the different portions of the modality specific circuitry.

The CDC 102 thus can provide one or more control signals to the filter networks 114 and 116 to adjust the transfer function and thereby establish a desired dynamic range for each respective channel. As a further example, the channel transfer function can be estimated a priori based on the configuration of the modality specific ($H_{CH}$) circuitry 104 and the intended of such circuitry. The channel transfer function ($H_{CH}$) for a given channel of the system 100 can be determined to provide a highest available dynamic range for a given modality. For example, the form of respective transfer function can be derived via appropriate simulation device (e.g., matlab). The transfer function can be programmed into the CDC 102, which can be further adjusted dynamically during operation, such as by adjusting respective filter coefficients and gain in the analog domain via control signal provided to the respective filter network 114 and 116. Additionally and alternatively, the CDC can adjust the transfer function in the digital domain (e.g., such as by programming the operation of the DSP 132).

By way of further example, the CDC 102 can include a filter control block 136 that is programmed and/or configured to set one or more filter coefficients associated with each of the filter networks 114 and 116 of the apparatus 100. Filter control 136 can provide the respective control signals through the corresponding digital-to-analog converters, indicated at 140 and 142, to set respective coefficients of the respective filter blocks 118 and 122. The filter coefficients can be selectively adjusted during operation to optimize the respective filter function based on the filter control 136 implemented by the CDC 102. The respective filter coefficients can be adjusted as a function of outputs computed by the DSP 132 for each of the respective channels. As one example, the coefficients associated with the filter networks 118 or 122 can be adjusted based on the operation of the channel, which further can vary according to biometric condition being monitored. The adjustments can be made dynamically based on the instantaneous DSP output or based on multiple DSP output samples acquired over a period of time (e.g., time averaged representation of the channel data). Alternatively or additionally, the filter control 136 can adjust filter coefficients for each channel based on the relative values of DSP outputs for a plurality of channels.

The CDC 102 can also include an amplifier control block 144 that is programmed and/or configured to provide a control signal for setting the gain of each of the respective amplifiers 120 and 124 associated with each respective channel. For example, the amplifier control block 144 can provide a gain value that is converted to a corresponding analog gain value by a corresponding digital to analog converters 146 and 148. The digital-to-analog converters 146 and 148 can provide corresponding gain for values, having respective voltage levels, adjusting the gain of the respective amplifiers 120 and 124. As one example, the amplifier control block 144 can set the respective gain for each respective channel in the modular apparatus 100 to achieve a maximum dynamic range of the data acquisition circuitry.

As mentioned above the initial transfer function for each respective channel in the modular apparatus 100 can be predetermined and programmed in the CDC 102. The CDC can employ the filter control 136 and amplifier control 144 to adjust the initial transfer function for increased efficiency and higher dynamic range for each of the respective channels in its operating environment. The transfer function for the modular apparatus 100 can vary according to the modality (e.g., type of sensor or therapy dispensing function associated with the modality specific circuitry 104). The filter coefficients and gain can be adjusted as discrete or continuous increments or decrements over a range of available settings. Additionally, the particular modality can be modified programmatically by the CDC 102, if necessary, and a new transfer function can be programmed at the CDC such as via the data bus programmed by a master module as described herein.

The transfer function can be programmed via the bus. Additionally or alternatively, a set of base transfer functions parameters can be programmed in memory (e.g., as a look-up table) of the CDC 102. For example, at start-up, a particular transfer function can be selected and set for each of the respective channels, such as based upon the function or purpose associated with the modality specific circuitry 104 and the status of the device 100. As mentioned above, each of the respective channels can have an initial starting transfer function that may be the same or different. As one example, it may be desirable, during operation, to replace leads or sensors for a given modality specific circuitry 104 with a different type of lead or sensor. In such a situation, the filter control 136 and amplifier control 144 of the CDC 102 can detect the variations in the received input signal from the DSP for the respective channel(s), and, in turn, implement appropriate changes to the transfer function, such as via adjustments to filter coefficients and/or the gain for the respective channel.

It will be appreciated that the functionality of DSP and CDC, while shown and described as being implemented by separate circuitry, can be integrated in single processor or an application specific circuit (ASIC) that can be programmed and configured to perform the combined functions. Those skilled in the art will further understand and appreciate that various implementations of modality specific circuitry that can also be integrated with one or both of the CDC and the DSP.

Figure 3:
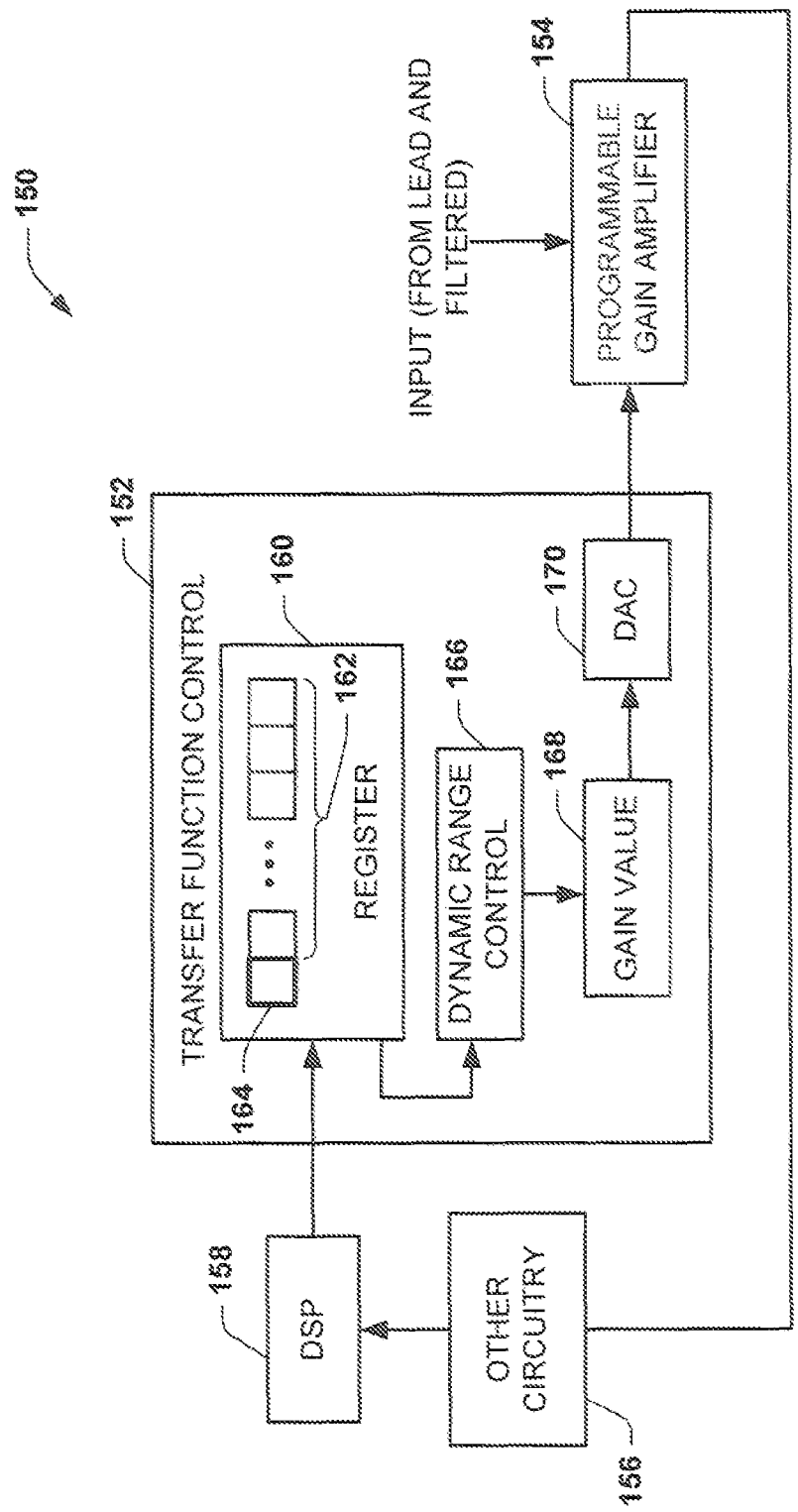
FIG. 3 depicts an example of transfer function control loop that can be implemented in a modular apparatus according to an aspect of the present invention.

FIG. 3 depicts an example of a transfer function control loop 150 that can be implemented according to one aspect of the invention. For instance, the control loop 150 can be employed to achieve a maximum dynamic range of associated conditions data acquisition circuitry for a given channel, such as a sensor and/or a therapy delivery device. The control loop 150 includes a transfer function control block 152 that is programmed and/or configured to adjust one or more parameters of a transfer function for the respective channel. As described herein, the transfer function can be derived as an aggregate transfer function corresponding to the respective portions of the modular apparatus.

In the example of FIG. 3, the given channel receives an input signal indicative of a conditions condition. The input signal, for instance, can be provided from a specially configured sensor via an electrical path (e.g., including a lead) to a programmable gain amplifier 154. The electrical path may also include other input circuitry (e.g., an analog isolation amplifier) which has been omitted from FIG. 3 for purposes of clarity. The programmable gain amplifier 154 receives the input and provides a corresponding amplified output signal to other circuitry 156. For example, the other circuitry 156 can include additional analog amplifiers as well as filtering circuitry, such as described herein. The other circuitry 156 also includes circuitry configured to perform analog-to-digital conversion on the amplified input signal. As described herein, analog-to-digital conversion can be performed by $\Sigma\Delta$ conversion to provide a corresponding high resolution digital output. While the example of FIG. 3 is shown and described in relation to a single channel, those skilled in the art will understand that a give modular apparatus can include appropriate circuitry for implementing transfer function control with respect to any number of one or more channels.

The corresponding digital representation of the amplified signal can be provided to a corresponding signal processor, such as a DSP 158. The DSP 158 is programmed and configured to compute a function from the digital representation provided by the other circuitry 156. The value of the computed function is provided to the transfer function control block 152. The transfer function control, for example, can include a register 160 configured and arranged for storing a predetermined number of bits. The register can be implemented in a separate register or in other types of memory configured for storing the digital value in a predetermined number of bits (e.g., in a predefined address space of RAM). As an example, one portion of the memory block, such as the least significant bits (LSB), indicated at 162, can have a word length or number of bits designed for accommodating the DSP output. Another portion of the register 1660, such as one or more of the most significant buts (MSB), indicated at 164, can be utilized for storing overflow bits(s). The transfer function control 152 can employ the overflow bit(s) 164 for determining adjustments to the transfer function.

A dynamic range control block 166 thus can be configured to control changes to the channel transfer function based on the compound value stored in the register 160. As one example, the dynamic range control 166 can increment or decrement a gain value 168 based on the value in the overflow data block 164. For instance, if the overflow data 164 indicates that the computed value provided by the DSP 158 indicates that available register space 162 has been exceeded, the dynamic range control 166 can decrement the gain value accordingly. In contrast, if the overflow data 164 is not indicative of the output of the DSP not filling the available space in the register, the dynamic range control 166 can cause an increase in the gain value 168. To mitigate fluctuations, the dynamic range control can implement adjustments based on a time-averaged value of the MSB 164.

The gain value 168 can be converted to a corresponding analog signal via a digital-to-analog converter (DAC) 170 that is utilized to program and set the gain of the programmable gain amplifier 154. For example, the analog output provided by the DAC can correspond to a gain factor that produces an increase or decrease in resolution of the input. The gain factor can be a continuous value or a selected set of discrete values (e.g., voltages), which further may vary according to the configuration of the programmable gain amplifier 154.

From the foregoing, it will be appreciated that the transfer function control loop 150 can operate to set the gain as to maximize the dynamic range of the date acquisition sensor that provides the input to the programmable gain amplifier 154. The transfer function control 152 can implement this process (e.g., adjustments to the channel transfer function) during a calibration phase, such as may occur at power up or reset. Alternatively or additionally, the transfer function control 152 can adjust the transfer function during normal operation, such as based on detecting variations in the value computed by the DSP 158 outside of expected operation parameters.

Those skilled in the art will understand and appreciate that a similar control loop can be utilized to set filter coefficients or other transfer function parameters based on the discussion contained herein. Such transfer function controls can be programmed in a CDC or other portion of the modular apparatus (e.g., the apparatus 100 of FIG. 2). Additionally, those skilled in the art will understand and appreciate that each respective active channel in a modular apparatus can implement a similar transfer function control to adjust the respective channel transfer function, including gain and filter coefficients associated with each transfer function. The particular controls further can vary according to the modality and biometric conditions being monitored or therapy being delivered by the modular apparatus.

Figure 4:
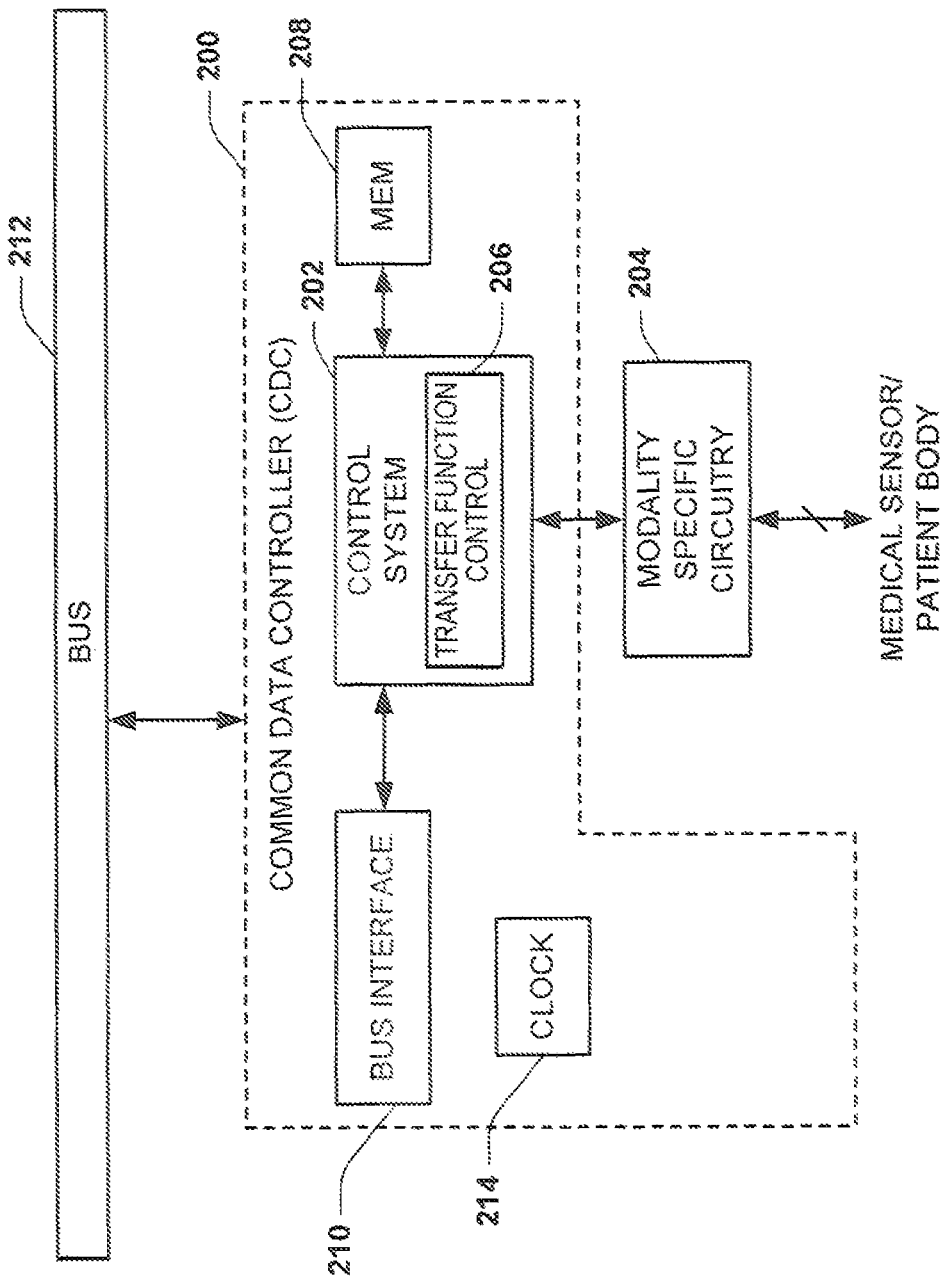
FIG. 4 depicts an example of a common data controller that can be implemented according to an aspect of the present invention.

FIG. 4 depicts an example of a common data controller (CDC) 200 that can be implemented in a modular apparatus in a system according to an aspect of the present invention. In the example of FIG. 4, the CDC includes a control system 202 that is programmed and configured to control operation of a modular apparatus. For example, the control system 202 can control one or more operating parameters associated with a modular specific circuitry 204. As described herein, for example, the control system 202 can include a transfer function control 206 that is programmed and/or configured to adjust one or more transfer function parameters, such as filter coefficients and/or gain values of a corresponding filter network during operation to maximize the dynamic range and performance of the modular apparatus. The transfer function control 206 can implement separate control for each respective channel transfer function according to the number of channels, configuration and intended use of the modality specific circuitry 204.

The control system 202 can implement instructions for implementing such control features based on instructions stored in associated memory 208. The memory can include non-volatile memory and/or volatile memory for storing appropriate executable instructions. Thus, the control system 202 may comprise a processor or control logic (not shown) for executing such instructions. The CDC 200 can also include a bus interface 210 that is utilized for transmitting and receiving data via an associated data bus 212. The data bus 212, for example, can be implemented as a backplane for communicating data relative (to and/or from) the CDC 200 and one or more other modules or devices (not shown, but see, e.g., FIG. 1) that may be connected the bus 212. The bus interface 210 thus is configured to facilitate such communication, such as having an input queue for receiving data from the bus and an output queue for transmitting data over the bus 212. Those skilled in the art will understand and appreciate various communication protocols and bus architectures that can be utilized.

For data to be transmitted over the bus, for example, the memory 208 can include a FIFO or other data structure that can be utilized for storing data from the modality specific circuitry. Such data in the FIFO can include calibration data associated with operation of the modular apparatus as well as biometric data acquired from one or more channels of the modality specific circuitry 204. As the FIFO or other data structure receives and is filled with data from the modality specific circuitry 204, the stored data can then be transmitted via the bus 212 to an associated destination module, such as a master module in the modular system.

Since each modular apparatus can be employed to acquire a different type of modular apparatus, the FIFO in the memory 208 may fill at different rate relative to a corresponding FIFO in a different modular apparatus. To accommodate such potentially varying acquisition rates, each FIFO can be configured to a memory size according to the type of modality (e.g., which defines its acquisition rate). A bus controller (not shown) can control the rate at which each modular apparatus transmits and receives data via the bus 212 in an asynchronous manner.

The CDC 200 further can include a clock 214 for controlling the timing of operation within the modular apparatus including the CDC 200 and the modality specific circuitry. Alternatively or additionally the modality specific circuitry can include its own clock for synchronizing timing of data acquisition from one or more acquisitions.

Figure 5:
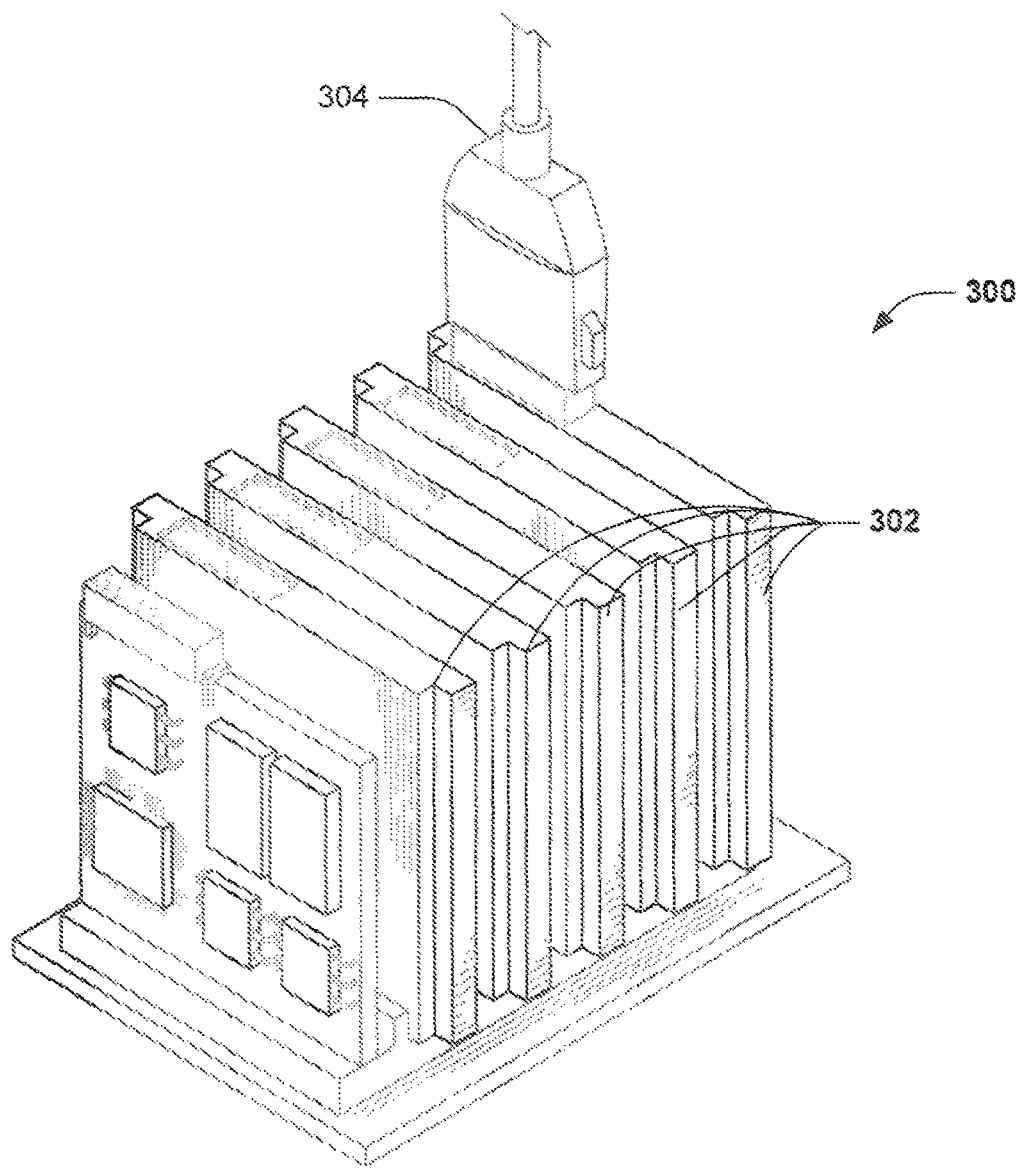
FIG. 5 depicts an example of a modular system that can be implemented according to an aspect of the present invention.

FIG. 5 depicts a perspective view of one example embodiment of a modular system 300 that can be constructed in accordance with an aspect of the invention. The modular system 300 includes a plurality of modular apparatuses 302 configured for performing desired functions such as described herein. For example, by replacing, inserting, swapping a set of one or more modular apparatuses 302, the modular system 300 can be configured to operate for acquisition of particular biometric data, control delivery of desired therapy and/or transmit data based on a particular transmission protocol. As one example, one or more of the modular apparatuses 302 in the modular system 300 can be adapted to acquire data related to electromyography (EMG, frequency range 2-500 Hz), electrocardiography (ECG, frequency range 0.05-100 Hz), resolution of 24 bits, electrocardiography (ECG, frequency range of 0.16-100 Hz), blood pressure, joint angle, pulse oximetry and the like. Each of the modular apparatuses 302 can be connected to the corresponding sensor(s) via an appropriate connector 304.

Each of the modular apparatuses 302 further can include one or more channels for acquiring and processing input signals indicative of corresponding biometric conditions. Each channel of each modular apparatus, for example, has a transfer function that can be adjusted independently, such as described herein, to achieve a desired dynamic range for data acquisition at a corresponding resolution. Additionally, different modular apparatuses, having different sensor requirements, can acquire data at different sample. For instance, asynchronous data collection can be implemented across modular apparatuses 302, while at the same time employing a synchronous clock within each modular apparatus to provide timing on module for data collection functions.

Figure 6:
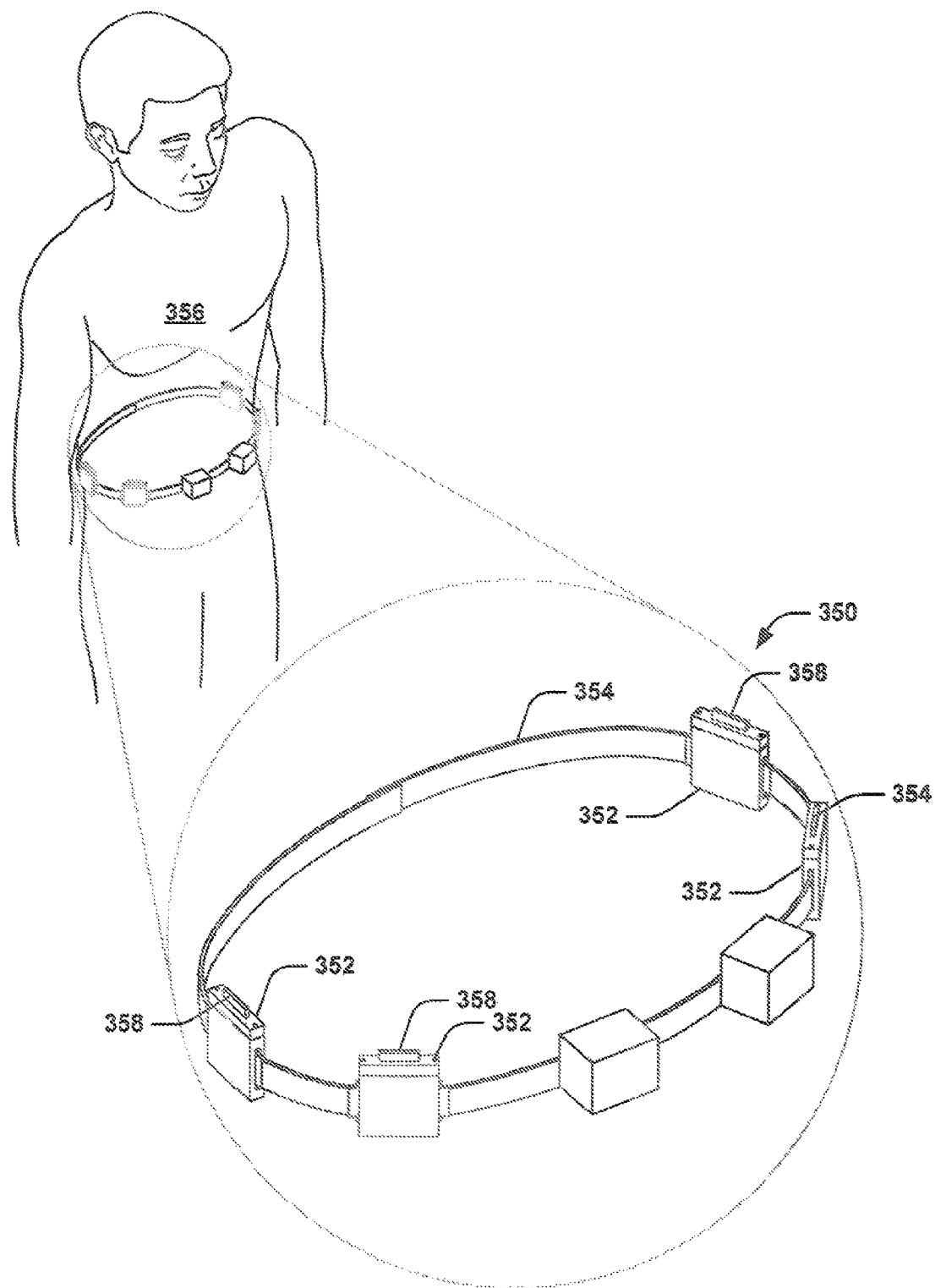
FIG. 6 depicts another example of a modular system that can be implemented according to an aspect of the present invention.

FIG. 6 depicts another embodiment of a modular system 350 that can be implemented according to an aspect of the invention. In the example of FIG. 6, the modular system 350 includes a plurality of modular apparatuses 352 spatially distributed along a common communication link (or bus) 354, such as can be implemented as part of a belt or harness attached to or disposed around the body of a user. While the communication link 354 is depicted as a belt in the example of FIG. 6, other types of harnesses (e.g., a chest harness, wrist band, arm band, a hat or the like) could be implemented. Certain modular apparatuses 352 can thus be located proximate to predetermined portions of a patient's body 356. Data can be communicated with such modular components 352 over a common communication link, or network, wherein all modules on the network communicate via a standard communications protocol. At least some of the modular apparatuses 352 include a modular component 358, which can be replaced, inserted or swapped for desired operation. Each modular component 358 has a form factor configured according to the requirements and interface provided at the apparatus 352.

In such a distributed system, one or more I/O modules are provided for interfacing with a process, wherein the outputs derive their control or output values in the form of a message from a master controller over the bus 354. For example, a modular component can receive an output value from a processor, via a communications network or a backplane communications bus. The desired output value for controlling a device associated with a given biometric condition can be generally sent to the output module in a message, such as an I/O message. The modular component that receives such a message can provide a corresponding output (analog or digital) to the controlled process. The modular component can also measure a value of a process variable and report the input values to a master controller or peer modular component over the network or backplane 354. The input values may be used by the master module for performing control computations.

Figure 7:
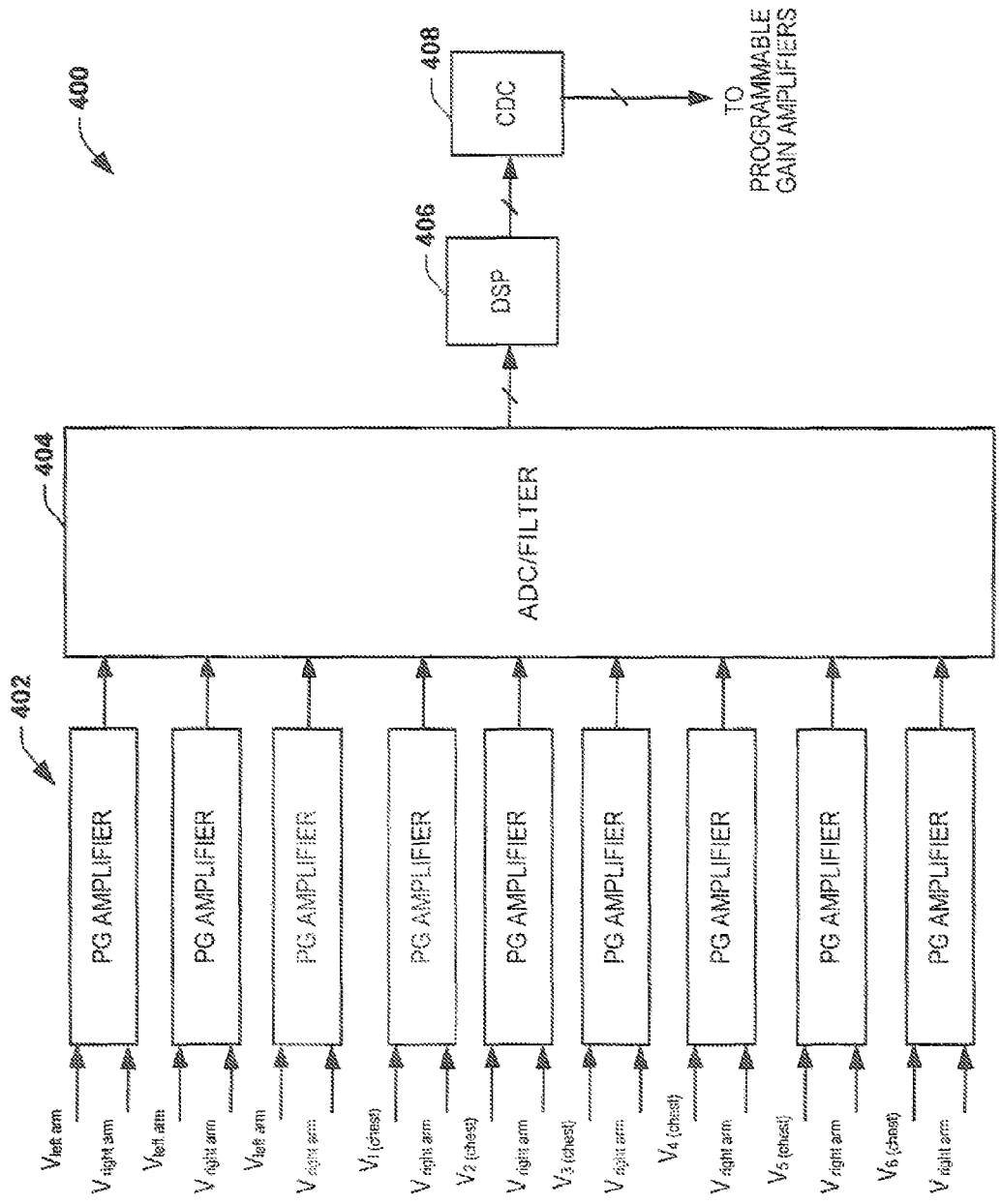
FIG. 7 depicts an example configuration for part of a modular aperture according to an aspect of the present invention.

FIG. 7 depicts one example block diagram of part of a modular apparatus 400 configured for acquiring ECG measurement data in accordance with an aspect of the invention. While the particular example of FIG. 7 shows an example configuration having a plurality of channels for acquiring ECG data, it will be appreciated that various other types and configurations of units can be provided according to an aspect of the invention.

In the example of FIG. 7, the modular apparatus 400 includes a plurality of programmable gain amplifiers 402 that receive respective channel inputs. The channel inputs further can go through additional analog circuitry (not shown), such as including filters and isolation amplifiers. The programmable gain amplifiers 402 provide corresponding amplified input signals to an ADC/filter block 404. The ADC/filter block converts the amplified inputs signals into corresponding digital representations, such as described herein. The ADC/filter block 404 provides the digital channel representation and provides the computed value to a CDC 408.

As described herein, each channel has a respective transfer function that can be adjusted. The CDC can provide a control signal for adjusting one or more parameters of each channel transfer function. For example, the CDC 408 performs transfer function control processes to adjust each channel transfer function dynamically, such as to achieve a maximum dynamic range. The CDC 408 thus provides a control signal to each of the programmable gain amplifiers 402 to adjust the gain according to the transfer function control performed on the computed value from the DSP 406. In addition, each channel can be individually configurable by the CDC 408, such as from 10 Hz sample rate, with a total maximum data throughput exceeding 32 kHz. Each channel thus can be provided with a desired dynamic range and operating frequency. Additionally, as described herein, each channel can have an individual set of programmable filters (e.g., programmable by the CDC 408) to allow for improved filtering and overall performance.

Figure 8:
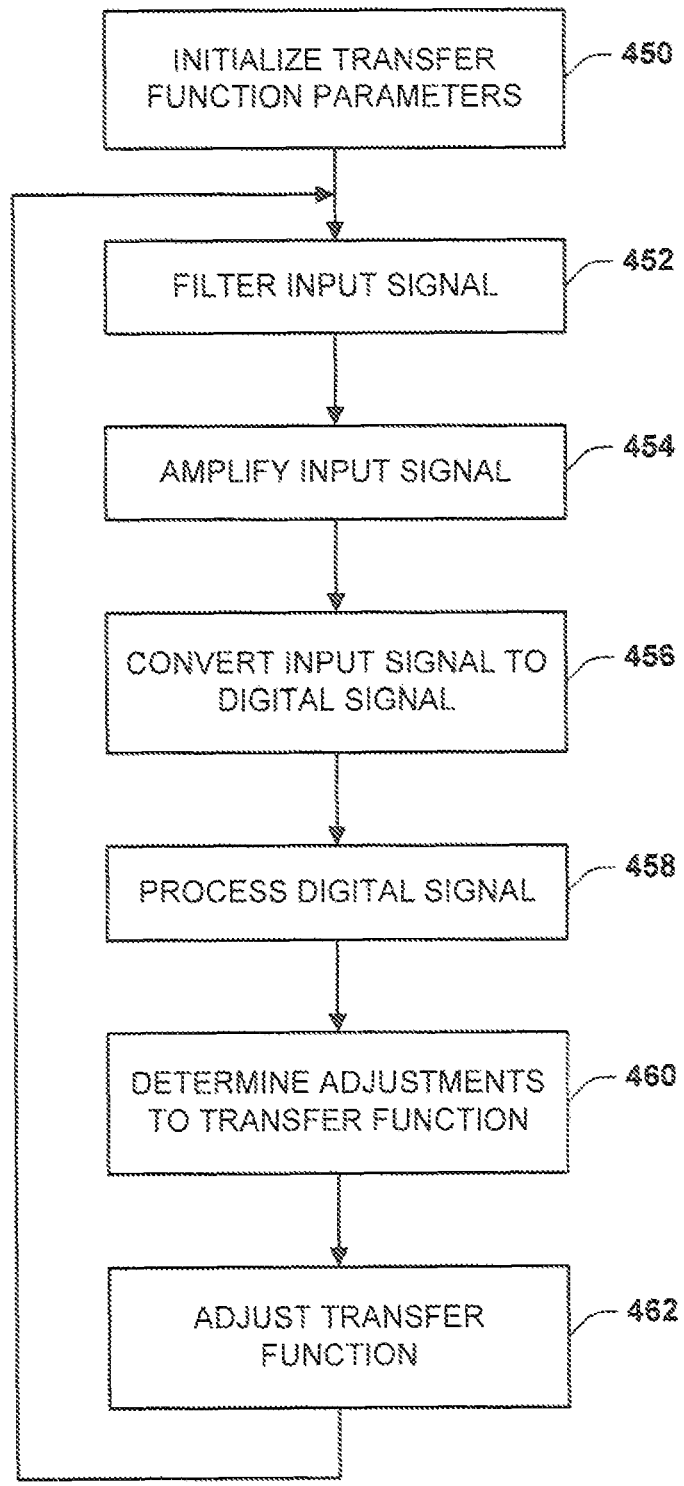
FIG. 8 is a flow diagram illustrating a method for controlling a transfer function for a modular system according to an aspect of the present invention.

In view of the structural and functional features described above, certain methods will be better appreciated with reference to FIG. 8. It is to be understood and appreciated that the illustrated actions, in other embodiments, may occur in different orders or concurrently with other actions. Moreover, not all features illustrated in FIG. 8 may be required to implement a method according to the subject invention. It is to be further understood that the following methodology can be implemented in hardware (e.g., one or more processors, such as in a computer or computers or in a biomedical device), software (e.g., stored in a computer readable medium or as executable instructions running on one or more processors), or as a combination of hardware and software.

FIG. 8 is a flow diagram depicting a method for adjusting a channel transfer function according to an aspect of the invention. The method can be implemented as part of a calibration phase or during normal operation. The method begins at 450 in which transfer function parameters are set to their starting values. For example, the starting values may be derived based on simulation or empirical studies for the modular apparatus and its intended modality. The starting values can thus be stored in memory of the modular apparatus.

At 452, a received input signal can be appropriately filtered to remove noise from the signal and other unwanted signal components. The filtering can be defined by programmable filter coefficients. At 454, the input signal is amplified by a programmable gain amplifier according to the gain value of the amplifier. The amplifier can include one or more gain stages, each of which may have a programmable gain.

At 456, the filtered and amplified signal is converted to a corresponding digital signal. For instance, the conversion can be implemented by a ΣΔ analog-to-digital converter to provide a high resolution digital output. At 458, the digital output can be processed (e.g., by a DSP) to provide an output value according to a predefined function. The function can be derived based on the transfer function determined for the channel. At 460, the computed output value can be evaluated to ascertain what adjustments, if any, are to be made to the channel transfer function. For instance, if the bit-length of the computed output value exceeds a predefined number of bits, the gain can be increased. If the bit-length is less than a minimum bit-length, the gain may be increased. The computed output value can also be analyzed relative to predetermined data (e.g., in a look-up table in memory of the CDC) to determine changes to filter coefficients. At 462, the transfer function can be updated based on the analysis at 460.

From 460, the method can return to 452 to continue the process such that the transfer function can be dynamically adjusted, such as to maintain a maximum dynamic range for circuitry associated with the input channel. It will be appreciated that, during normal operation, the process may repeat periodically at a predefined timing interval. Alternatively, the CDC may routinely monitor parameters and trigger adjustments when such parameters are outside of expected operating parameters.

Although the innovation has been shown and described with respect to certain examples and embodiments, it will be appreciated that equivalent alterations and modifications will occur to others skilled in the art upon reading and understanding this description and drawings. Accordingly, the invention is intended to embrace all such alterations, modifications and variations that fall within the scope of the appended claims. In particular regard to the various functions performed by the above described components (assemblies, devices, circuits, systems, etc.), the terms (including a reference to a "means") used to describe such components are intended to correspond, unless otherwise indicated, to any component which performs the specified function of the described component (e.g., that is functionally equivalent), even though not structurally equivalent to the disclosed structure, which performs the function in the herein illustrated exemplary aspects of the innovation. Furthermore, to the extent that the terms "includes", "including", "has", "having", and variants thereof are used in either the detailed description or the claims, these terms are intended to be inclusive in a manner similar to the term "comprising." In the claims, unless otherwise indicated, the article "a" is to refer to "one or more than one."

What is claimed is:

1. A modular apparatus for acquiring biometric data, the modular apparatus comprising:
   circuitry operative to receive an input signal at an input corresponding to the biometric data, the circuitry comprising at least one filter and an amplifier, the circuitry being configured to process the input signal according to an aggregate transfer function thereof and to provide a corresponding processed input signal, the biometric data being indicative of at least one of (i) biological or biomedical information of a patient acquired from one or more physiological sensors, (ii) feedback information associated with a delivery of a therapy to the patient (iii) status information for the one or more physiological sensors, or (iv) operating parameters associated with equipment used to deliver the therapy to the patient;
   a controller configured to provide at least one control signal to the circuitry to programmatically modify the transfer function of the modular system by setting (i) at least one filter coefficient of the at least one filter and (ii) a gain of the amplifier to facilitate acquisition of the biometric data; and
   a register configured for storing a digital representation of the corresponding processed signal in a predetermined number of bits assigned to store the biometric data acquired by the circuitry, the controller being configured to set the at least one filter coefficient and the gain of the aggregate transfer function so that the register accommodates a maximum dynamic range of the circuitry by fitting the biometric data in the predetermined number of bits.

2. The apparatus of claim 1, wherein the input circuitry comprises at least one amplifier, the at least one amplifier having a programmable gain that is dynamically adjusted by the control signal to amplify the input signal and thereby acquire the biometric data with maximum resolution.

3. The apparatus of claim 1, wherein at least one overflow bit of the register indicates that the dynamic range exceeds a size of another portion of the register, the apparatus further comprising a dynamic range control that adjusts a gain value based on the at least one overflow bit of the register, the controller providing the control signal according to the gain value.

4. The apparatus of claim 1, further comprising a signal processor that computes a sensor signal value for the digital representation of the corresponding processed signal by applying a predefined function to a representation of the corresponding sensor signal.

5. The apparatus of claim 4, the controller setting a gain of at least a portion of the circuitry so that the sensor signal value is accommodated in the register with a maximum resolution defined by the dynamic range of the circuitry.

6. The apparatus of claim 1, wherein the circuitry comprises a plurality of analog circuits, each having a component transfer function that forms part of an aggregate channel transfer function for a given channel of the modular apparatus, the component transfer function of at least one of the plurality of analog circuits for the given channel being adjusted based on the at least one control signal.

7. The apparatus of claim 6, wherein at least one of the plurality of analog circuits further comprises a programmable gain amplifier that amplifies the sensor signal according to gain setting of the respective programmable gain amplifier, the controller providing a gain control signal to set the gain setting of the respective programmable gain amplifier and thereby change the channel transfer function.

8. The apparatus of claim 7, wherein at least one of the plurality of analog circuits further comprises at least one analog filter for filtering the sensor signal according to filter coefficients of the filter, the controller providing a filter control signal to set the filter coefficients of the filter and thereby change the channel transfer function.

9. The apparatus of claim 1, further comprising modality specific circuitry configured for collecting and storing biometric data, corresponding to the input signal, at a predetermined acquisition rate that is set according to a type of the biometric data, the input circuitry being part of the modality specific circuit and being responsive to the at least one control signal.

10. A modular apparatus for acquiring biometric data, the modular apparatus comprising:
    circuitry operative to receive an input signal, the circuitry being configured to process the input signal according to a transfer function thereof and to provide a corresponding processed input signal;
    a controller configured to provide at least one control signal to the circuitry to programmatically modify the transfer function of the modular system to facilitate acquisition of the biometric data, the biometric data being indicative of at least one of (i) biological or biomedical information of a patient acquired from one or more physiological sensors, (ii) feedback information associated with a delivery of a therapy to the patient (iii) status information for the one or more physiological sensors or (iv) operating parameters associated with equipment used to deliver the therapy to the patient; and
    a plurality of channels, each channel having circuitry for receiving and processing a respective input signal, the controller selectively adjusting more than a gain setting of a channel transfer function associated with the circuitry of each respective channel of the plurality of channels to maximize the dynamic range of each respective channel according to a predetermined portion of addressable memory space assigned to each respective channel.

11. The system of claim 10, wherein each of the plurality of channels has a sample rate that is individually configurable by the controller.

12. A modular system for acquiring biometric data comprising:
    means for amplifying an input signal received at an input to provide an amplified signal;
    means for filtering the input signal to provide a filtered signal;
    means for processing the amplified and filtered signal to provide a computed value corresponding to the biometric data, the biometric data being indicative of at least one of (i) biological or biomedical information of a patient acquired from one or more physiological sensors, (ii) feedback information associated with a delivery of a therapy to the patient (iii) status information for the one or more physiological sensors or (iv) operating parameters associated with equipment used to deliver the therapy to the patient;
    means for controlling a transfer function of at least the means for amplifying and the
    means for filtering based on the computed value; and
    means for storing a digital representation of the computed value in a predetermined amount of memory space, the means for controlling adjusts the transfer function for accommodation of the digital representation of the computed value in the means for storing to achieve a maximum dynamic range for the modular system.

13. The system of claim 12, wherein the means for controlling adjusts a gain value of the means for amplifying based on a word size of the computed value relative to available space in the means for storing.

14. The apparatus of claim 12, wherein the means for processing further comprises means for applying a predefined function to a representation of the corresponding input signal to provide the computed value.

15. The apparatus of claim 12, further comprising a plurality of input channels, each of the plurality of input channels comprising means for amplifying a corresponding input signal, each of the plurality of input channels having a respective channel transfer function that is adjustable by the means for controlling.

16. The system of claim 15, wherein each of the plurality of channels comprises other circuitry having a respective transfer function that, in conjunction with a transfer function component of the means for amplifying, defines the channel transfer function.

17. The system of claim 16, wherein each of the plurality of input channels further comprises means for filtering the input signal for the respective channel, which contributes to the channel transfer function according to the filtering, and the filtering performed by the means for filtering for each of the plurality of channels being controlled by the means for controlling.

* * * * *